United States Patent [19]

Holland et al.

[11] 4,237,060

[45] Dec. 2, 1980

[54] PROSTACYCLIN ANALOGS

[75] Inventors: George W. Holland; Perry Rosen, both of North Caldwell, N.J.

[73] Assignee: Hoffmann-La Roche Inc., Nutley, N.J.

[21] Appl. No.: 23,116

[22] Filed: Mar. 23, 1979

[51] Int. Cl.$^3$ .......................................... C07D 307/935
[52] U.S. Cl. ................................ 260/346.22; 425/285
[58] Field of Search .................................... 260/346.22

[56] References Cited

U.S. PATENT DOCUMENTS

| 4,123,441 | 10/1978 | Johnson | 260/346.22 |
| 4,125,712 | 11/1978 | Axen | 260/346.22 |

FOREIGN PATENT DOCUMENTS

| 855224 | 11/1977 | Belgium . |
| 860278 | 4/1978 | Belgium . |
| 862514 | 4/1978 | Belgium . |
| 7705105 | 6/1978 | South Africa . |

*Primary Examiner*—Henry R. Jiles
*Attorney, Agent, or Firm*—Jon S. Saxe; Bernard S. Leon; William H. Epstein

[57] ABSTRACT

The prostacyclins 6,9-epoxy-16-substituted-15-hydroxyprost-(13E)-enoic acids and esters useful as antisecretory agents, blood pressure lowering agents, antiulcerogenic agents, antihypertensive agents, bronchodilation agents and for combating gastrohyperacidity and as anti-blood platelet aggregating agents.

17 Claims, No Drawings

PROSTACYCLIN ANALOGS

SUMMARY OF INVENTION

In accordance with this invention, compounds of the formula:

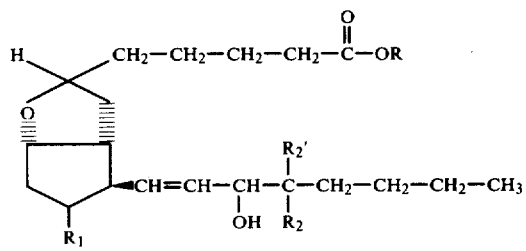

wherein R is hydrogen or lower alkyl; R is hydrogen, lower alkyl, hydroxymethyl,

or $R_2$ is hydrogen, lower alkyl or fluoro; and $R_2'$ is fluoro, trifluoromethyl, or lower alkyl and the dotted bond is optionally hydrogenated and with the proviso that when $R_1$ is hydrogen, $R_2'$ is trifluoromethyl and with the further proviso that when $R_2$ is fluoro, $R_2'$ is lower alkyl or fluoro, and their optical antipodes and racemates are useful as antisecretory agents, antihypertensives, antiulcerogenic agents, blood pressure lowering agents and for combatting gastrohyperacidity and for anti-blood platelet aggregating agents.

The compounds of formula I are prepared from compounds of the formula:

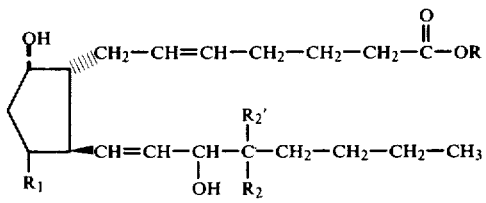

wherein $R, R_1, R_2$ and $R_2'$ are as above.

DETAILED DESCRIPTION OF THE INVENTION

As used throughout this application, the term "lower alkyl" includes both straight chain and branched chain alkyl groups having from 1 to 7 carbon atoms such as methyl and ethyl. As also used herein, the term "lower alkanoic acids" comprehends an alkanoic acid of 1 to 7 carbon atoms such as formic acid and acetic acid. As further used herein, the term "halogen" or "halo", unless otherwise stated, comprehends fluorine, chlorine, bromine and iodine. Alkali metal includes all alkali metals such as lithium, sodium and potassium.

In the process of this invention, all compounds having one or more asymmetric carbon atoms can be produced as racemic mixtures. These racemic mixtures which are obtained can be resolved at the appropriate steps in the process of this invention by methods well known in the art whereupon subsequent products may be obtained as the corresponding optically pure enantiomers. On the other hand, the claimed optically active enantiomer or racemates of formula I can be produced depending upon the optical form of the compound of formula II utilized as a starting material.

In the pictorial representation of the compounds given throughout this application, a thickened taper line (▼) indicates a substituent which is in the beta-orientation (above the plane of the molecule), a dotted line (||||) indicates a substituent which is in the alpha-orientation (below the plane of the molecule) and a wavy line (∿) indicates a substituent which is in either the alpha- or beta-orientation or mixtures of these isomers. It is to be understood that the pictorial representations of the compounds given throughout the specification are set forth for convenience and are to be construed as inclusive of other forms including enantiomers and racemates and are not to be construed as limited to the particular form shown.

As also used herein, the term "aryl" signifies mononuclear aromatic hydrocarbon groups such as phenyl, tolyl, etc and polynuclear aryl groups such as naphthyl, anthryl, phenanthryl, azulyl, etc. The preferred aryl group is phenyl, or tolyl.

The compounds of formula I as well as their optical antipodes and racemates are active as anti-secretory agents, bronchodilaters, anti-blood platelet aggregators, anti-ulcerogenic agents, anti-hypertensive agents and blood pressure lowering agents.

The compounds of formula I wherein $R_2'$ is fluoro or trifluoromethyl, i.e. compounds of the formula:

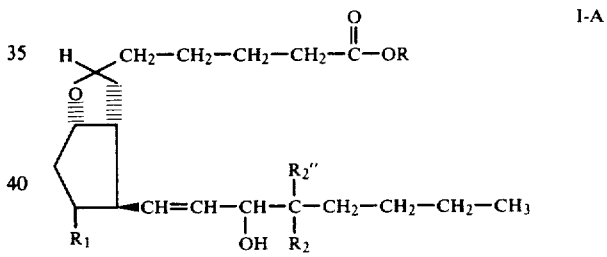

wherein R, $R_1$ and $R_2$ are as above; and $R_2''$ is fluoro, or trifluoromethyl and the dotted bond is optionally hydrogenated and with the proviso that when $R_1$ is hydrogen, $R_2''$ is trifluoromethyl; and with the further proviso that when $R_2$ is fluoro, $R_2''$ is fluoro as well as their optical antipodes or racemates are particularly useful as antihypertensive and blood pressure lowering agents.

The compounds of formula I where $R_2$ is hydrogen or lower alkyl and $R_2'$ is lower alkyl, i.e. compound of the formula:

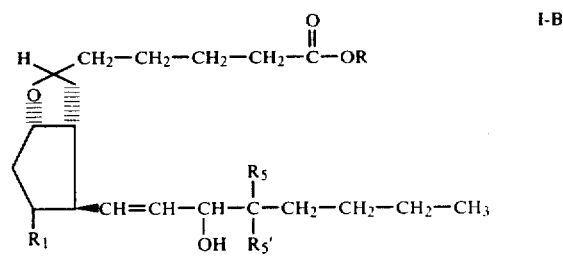

wherein R and $R_1$ are as above; $R_5$ is hydrogen or lower alkyl and $R_5'$ is lower alkyl; and the dotted bond is optionally hydrogenated and with the proviso that $R_1$ is other than hydrogen,
as well as their optical antipodes and racemates thereof are especially useful as anti-secretory and anti-ulcerogenic agents.

That the compounds of this invention are active as blood pressure lowering agents can be seen from the administration of [6S,8R,9S,11R,12S,15R,16R]-6,9-epoxy-11-methyl-16-fluoro-15-hydroxyprost-(13E)-enoic acid [Compound A] by the following test:

Charles River male rates weighing 170-210 grams are used in the present study. DOCA-Na hypertension is induced in these rats by unilateral mephrectomy followed by subcutaneous implantation of a 25 mg deoxycorticosterone acetate pellet. Animals are placed in individual cages and receive 0.9% by weight sodium chloride aqueous solution and rat chow diet ad libitum. Two weeks are allowed to elapse from the time of surgery for development of hypertension, i.e. systolic blood pressure above 150 mmHg. Systolic blood pressure is measured indirectly from the tail of unanesthetized rats (restrained in holders heated for 5-10 minutes at 37°-38° C.) using a pneumatic pulse transducer (piezoelectric crystal and occluding cuff). The transducer and occluding cuff are coupled to a two-channel recorder. Control readings are taken prior to drug and at 1, 3, 6, 24, 48 and 72 hours post administration of drug. All drugs are prepared fresh in a polyethylene glycol (mw=400) and orally administered to rats. The placebo that was used was polyethylene glycol (mw=400). It was found that the effective dose [$ED_{40}$] of compound A which produced a 40 mmHg decrease in systolic blood pressure 24 hours after administration was 8.6 mg/kg p.o.

That the compounds of this invention are active as anti-secretory and anti-ulcerogenic agents can be seen by administering [6S,8R,9S,11R,12S,15R] methyl-6,9-epoxy-11,16,16-trimethyl-15-hydroxyprost(13E)-enoate (Compound B) by the following test:

Compound B was tested as gastric secretory depressants in the unanesthetized rat with acute gastric fistula. On the day prior to the experiment, fasted female rats (average weight 250 g) were surgically catheterized in the inferior vena cava (for the constant infusion of saline and administration of compounds), the common bile duct (to divert bile and pancreatic secretions which may reflux causing contamination of gastric contents), the forestomach (for infusion of a small volume of water during the experiment) and the glandular stomach (for the collection of gastric contents and their continuous monitoring by means of a pH microelectrode). On the day of the experiment, water infusion through the stomach (for the collection of gastric contents and their continuous monitoring by means of a pH microelectrode). On the day of the experiment, water infusion through the stomach was begun for a period of 60 minutes prior to drug administration. During this baseline period, the pH of the secretory flow was about 1.5 for each animal. Individual samples were collected at 10-minute intervals during this baseline period to monitor the pH. The compound dissolved in polyethylene glycol (average molecular weight of about 400) was administered intravenously (i.v.), after this baseline period and samples were continuously collected for 60 minutes. The samples of gastric contents were subsequently assayed for pH, volume, total acid content ($\mu$Eq/ml) and total acid output for 10 minutes ($\mu$Eq/10 minutes). Results showed that the acid concentrations ($\mu$Eq/ml) was inhibited by a maximum of 52% at 55 minutes after administration of Compound B in a dose of 40 $\mu$g/kg i.v. Also at this dose, the acid output ($\mu$Eq/10 ml) was inhibited by a maximum of 72%, 55 minutes after drug administration.

The compounds of formula I can be used by the pharmaceutical and veterinary arts in a variety of pharmaceutical or veterinary preparations. In these preparations, the new compounds are administerable in the form of tablets, pills, powders, capsules, injectables, solutions, suppositories, emulsions, dispersions, feed premixes and in other suitable forms. The pharmaceutical or veterinary preparations which contain the compound of formula I are conveniently admixed with a non-toxic pharmaceutical organic carrier or a non-toxic pharmaceutical inorganic carrier. Typical of pharmaceutically acceptable carriers are, for example, water, gelatin, lactose, starches, magnesium stearate, talc, vegetable oils, polyalkylene glycols, petroleum jelly and other conventionally employed pharmaceutically acceptable carriers. The pharmaceutical preparations may also contain non-toxic auxiliary substances such as emulsifying, preserving and wetting agents and the like, as for example, sorbitan monolaurate, triethanol amine oleate, polyoxyethylene sorbitan, dioctyl sodium sulfosuccinate and the like.

The daily dose administered for the comounds will, of course, vary with the particular novel compounds employed because of the very potency of the compounds, the chosen route of administration and the size of the recipient. The dosage administered is not subject to definite bounds but it will usually be in effective amounts of the pharmacologically function of the prostacyclin. Representation of a typical method for administering the prostacyclin compounds of formula I is by the injectable type administration route. By this route, a sterile solution containing the prostaglandin of formula I can be administered intraveneously at the rate of 0.1 microgram to 0.30 micrograms per day per kilogram of body weight.

For administering the compounds of formula I to domestic animals or laboratory animals, the compounds are prepared in the form of a food pre-mix such as mixing with dried fish meal, oatmeal and the like and the prepared pre-mix is added to a regular feed thereby administering the compound to the domestic or laboratory animal in the form of a feed.

The compound of formula I includes the compound of formula I in its 6R configuration, i.e. a compound of the formula

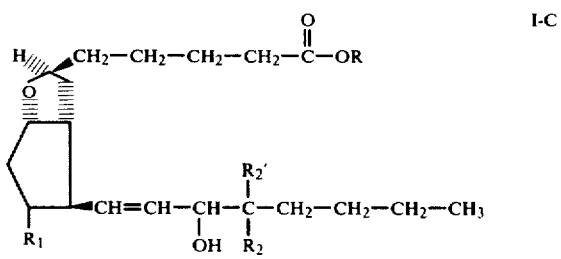

wherein R, $R_1$, $R_2$ and $R_2'$ as above, and with the proviso that when $R_1$ is hydrogen, $R_2'$ is trifluoromethyl; and with the further proviso that when $R_2$ is fluoro; $R_2'$ is lower alkyl, and the dotted bond is optionally saturated as well as the compound of formula I in its 6S form, i.e. a compound of the formula:

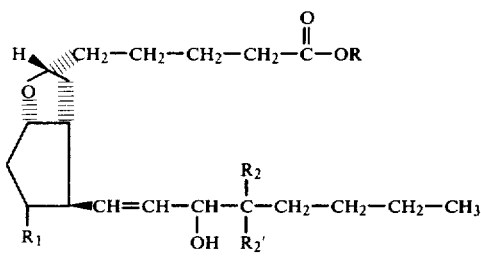

I-D wherein R, $R_1$, $R_2$ and $R_2'$ are as above and the dotted bond is optionally saturated and with the proviso that when $R_1$ is hydrogen, $R_2'$ is trifluoromethyl; and with the further proviso that when $R_2$ is fluoro, $R_2'$ is lower alkyl, and the dotted bond is optionally saturated as well as mixtures of the compounds of formulas I-C and I-D. The compounds of formula I-C are preferred.

Depending upon the particular form of the compound of formula I desired, the compound of formula II which is utilized as a starting material can be either a racemate or can be in the form of its optical antipodes.

The compound of formula I wherein $R_1$ is hydrogen, hydroxymethyl or lower alkyl and the dotted bond is not hydrogenated is formed from the compound of formula II via the following intermediate:

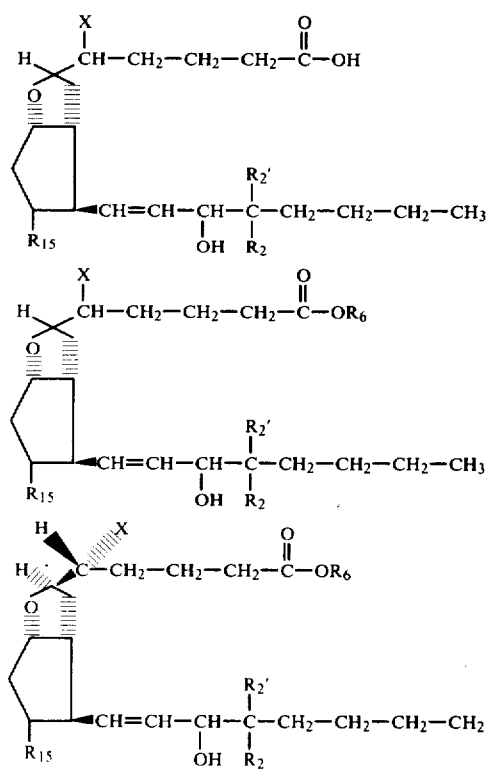

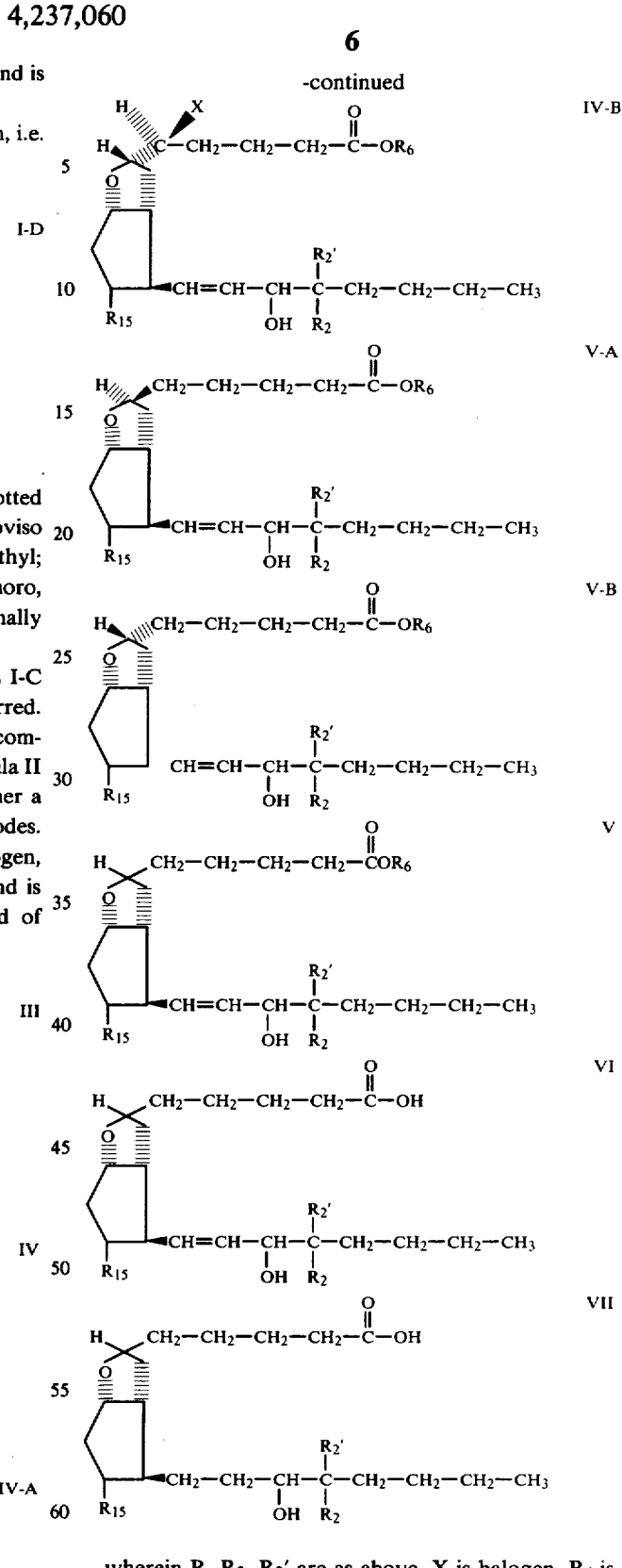

wherein R, $R_2$, $R_2'$ are as above, X is halogen, $R_6$ is lower alkyl; $R_{15}$ is hydrogen, hydroxymethyl or lower alkyl, with the proviso that when $R_{15}$ is hydrogen, $R_2'$ is trifluoromethyl with the further proviso that when $R_2$ is fluoro, $R_2'$ is lower alkyl or fluoro.

The compound of formula II is converted to the compound of formula III by hydrohalogenation. Any conventional method of hydrohalogenation can be utilized in carrying out this reaction. Among the preferred methods of hydrohalogenation is by treating the compound of formula II with a hydrohalogenating agent, such as N-halosuccinimides. Generally, this reaction is carried out in the presence of a halogenated hydrocarbon solvent such as methylene chloride, ethylene chloride, etc. In fact, any conventional halogenated hydrocarbon solvent can be utilized. In carrying out this reaction, temperatures of from 0° to 35° C. can be utilized. Generally it is preferred to carry out this reaction at room temperature.

The compound of formula III is converted to the compound of formula IV by esterification with a lower alkanol or a reactive derivative of a lower alkanol. Any of the conventional reactive derivatives of lower alkanol such as a lower alkyl halide, diazoalkanes including diazomethane can be utilized in carrying out this reaction. Any conventional method of esterification utilizing lower alkanols or reactive derivatives thereof can be utilized in converting the compound of formula III to the compound of formula IV. If desired, the compound of formula IV can be separated to the compound of formula IV-A and IV-B. By utilizing this reaction scheme, the compound of formula IV-A will be converted to the compound of formula I-C and the compound of formula IV-B will be converted to the compound of formula I-D. On the other hand, the compound of formula IV can be converted by the subsequent reactions directly into the compound of formula I through the intermediate of formula V. The separation of the compound of formula IV into its isomers, i.e. the compound of formula IV-A and IV-B can be carried out by conventional methods of separation such as chromatography. Any conventional method of separating the isomers can be utilized in carrying out the separation of the compound of formula IV into the compound of formula IV-A and IV-B.

The compound of formula IV can be converted to the compound of the formula V by treatment with a trialkyl tin hydride or triaryl tin hydride. Any conventional trialkyl or triaryl tin hydride can be utilized in this reaction. Among the preferred tin hydrides are the trilower alkyl tin hydrides such as tributyl tin hydride. Among the preferred triaryl tin hydrides is triphenyl tin hydride. On the other hand, this reaction can be carried out by generating the triaryl or trialkyl tin hydride in situ. This is carried out by utilizing a triaryl tin chloride or tributyl tin chloride in the presence of an alkali metal borohydride. The alkali metal borohydride converts to tri(aryl or alkyl) tin chloride to the corresponding tin hydride. The trialkyl or triaryl hydride is present in the conversion of the compound of formula IV to the compound of formula V either in molar amount or in catalytic quantities. This reaction is carried out in an inert organic solvent. Any conventional inert organic solvent can be utilized. Among the preferred inert organic solvents are the hydrocarbon solvents such as the aliphatic and aromatic hydrocarbon solvents. Solvents such as hexane, octane, toluene, benzene, etc. are especially preferred. This reactiion can be carried out at room temperature and atmospheric pressure. On the other hand, elevated and reduced pressures can be utilized with temperatures of from 20° to 80° C. being generally preferred. The most preferred embodiment of this reaction is carrying this reaction out at reflux. If desired, a free radical initiator can be utilized in carrying out this reaction. Any conventional free radical initiator can be utilized in carrying out this reaction. Among the preferred free radical initiators are benzoyl oxide and 2,2'-azobis (2-methylpropionitrile). The presence of a free radical initiator can speed up the rate of reaction period. If the compound of formula IV-A is utilized, this reaction will produce the corresponding isomer of the compound of formula V, i.e., the compound of formula V-A. On the other hand, if the compound of formula IV-B is utilized, the corresponding isomer of the compound of formula V will be produced, i.e., the compound of formula V-B.

The compound of formula V is converted to the compound of formula VI by basic hydrolysis. This reaction also converts to the compound of formula V-A to the corresponding isomers of the compound of formula VI. Any conventional method of basic hydrolysis such as treating the compound of formula V with an aqueous alkali metal hydroxide solution can be utilized to affect this conversion.

Either the compound of formula V or VI can be converted to the compound of formula VII by hydrogenation utilizing a conventional hydrogenation catalyst such as platinium oxide. Any of the conditions conventional in catalytic hydrogenation can be utilized in this reaction. In like manner, the corresponding isomers of compounds of the formula V or VI can be converted to the corresponding isomer of the compound of formula VII.

Where $R_1$ in the compound of formula I is

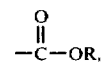

this compound can be prepared via the following intermediates:

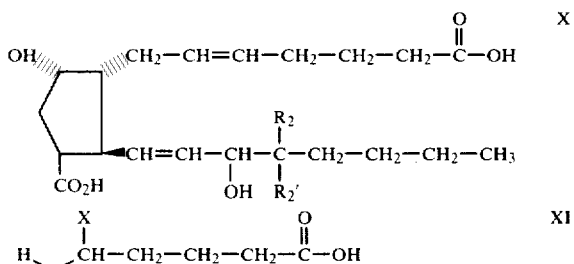

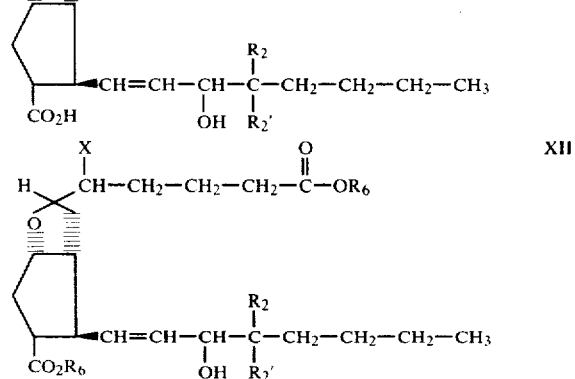

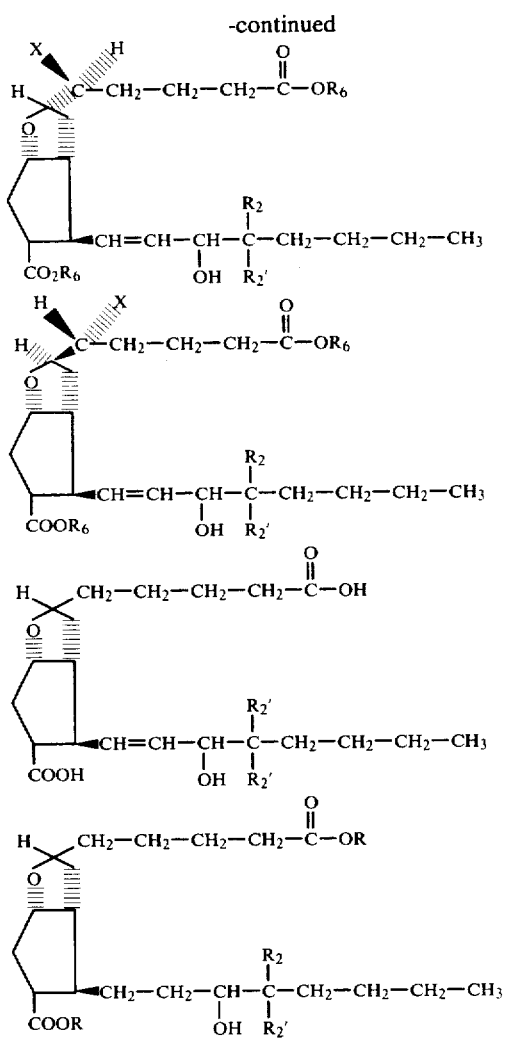

wherein X, R, $R_2$, $R_2'$ and $R_6$ are as above, with the priviso that when $R_2$ is fluoro, $R_2'$ is lower alkyl or fluoro.

The compound of formula X is converted to the compound of formula XI by treatment with a hydrohalogenating agent in the same manner as described with respect to the conversion of a compound of the formula II to a compound of the formula III. The compound of formula XI is converted to the compound of formula XII by esterification such as described hereinbefore in connection with the conversion of a compound of the formula III to a compound of the formula IV. The compound of formula XII can be separated, if desired, into its two isomers, i.e. the compound of formula XII-A and the compound of formula XII-B. This separation is carried out in the same manner as described hereinbefore in connection with the separation of the compound of formula IV to the compound of formula IV-A and IV-B. In like manner, the compound of formula XII can be converted to the compund of formula XIII and XIV. On the other hand, the isomers of formula XII-A and XII-B can be converted into the corresponding isomers of the compounds of formula XIII and the compounds of formula XIV, without changing the centers of asymmetry.

The compound of formula XII is converted to the compound of formula XIII by treatment with a trialkyl tin hydride or a triaryl tin hydride in the same manner as described in converting the compound of formula IV to the compound of formula V. In this manner, the compound of formula XIII is produced. If desired, the compound of formula XIII can be esterified so that both free carboxyl groups are esterified with a lower alkanol. Any conventional method of esterification such as mentioned hereinbefore can be utilized to produce the compound of formula XIII wherein R is lower alkyl. The compound of formula XIII either containing the free carboxyl or esterified carboxyl groups can be converted to the compound of formula XIV by catalytic hydrogenation. This catalytic hydrogenation can be carried out in the manner described hereinbefore.

Where R in the compound of formula I is hydrogen, the novel compounds of this invention include the pharmaceutically acceptable salts thereof. Among the preferred pharmaceutically acceptable salts are the alkali metal salts such as potassium, sodium and lithium. Another pharmaceutically acceptable salt for use in accordance with this invention are the ammonium salts. In accordance with this invention, any conventional pharmaceutically acceptable salt can be utilized.

The invention is further illustrated by the following examples. These examples are illustrative but not limitative of the claimed invention. As utilized in the examples, the term "Sephadex LH-20" is a bead-form dextran gel having hydroxy propyl groups attached to the ether linkages in the glucose units of the dextran chains.

EXAMPLE 1

[5R,6R,8R,9S,11R,12S,15R,16R]Methyl 5-iodo-6,9-epoxy-11-methyl-16-fluoro-15-hydroxy-prost-(13E)-enoate and [5S,6S,8R,9S,11R,12S,15R,16R]Methyl-5-iodo-6,9-epoxy-11-methyl-16-fluoro-15-hydroxyprost-(13E)-enoate To a solution of 1.0 g of [8R,9S,11R,12S,15R,16R]-11-methyl-16-fluoro-9,15-dihydroxyprosta-(5Z),(13E)-dienoic acid in 10 ml of methylene chloride was added 0.67 g of N-iodosuccinimide. After stirring for one hour at room temperature, 50 ml of diethyl ether was added and the solution was washed with dilute aqueous sodium thiosulfate. The organic layer was dried (MgSO$_4$) and the solvent removed by rotary evaporation at reduced pressure to give 1.2 g of a mixture of [5R,6R,8R,9S,11R,12S,15R,16R]-5-iodo-6,9-epoxy-11-methyl-16-fluoro-15-hydroxyprost-(13E)-enoic acid and [5S,6S,8R,9S,11R,12S,15R,16R]-5-iodo-6,9-epoxy-11-methyl-16-fluoro-15-hydroxyprost-(13E)-enoic acid. This mixture was dissolved in 25 ml of diethyl ether and treated at 0° C. with an excess of an ethereal solution of diazomethane. After stirring for one hour, the volatiles were removed by rotary evaporation and the residual materials were purified by silica gel chromatography to give 0.62 g of [5R,6R,8R,9S,11R,12S,15R,16R]methyl 5-iodo-6,9-epoxy-11-methyl-16-fluoro-15-hydroxy-prost-(13E)-enoate and 0.38 g of [5S,6S,8R,9S,11R,12S,15R,16R]methyl 5-iodo-6,9-epoxy-11-methyl-16-fluoro-15-hydroxyprost-(13E)-enoate.

EXAMPLE 2

[6S,8R,9S,11R,12S,15R,16R]Methyl 6,9-epoxy-11-methyl-16-fluoro-15-hydroxyprost-(13E)-enoate To a solution of 1.0 g of [5R,6R,8R,9S,11R,12S,15R,16R]-methyl 5-iodo-6,9-epoxy-11-methyl-16-fluoro-15-hydroxyprost-(13E)-enoate in 50 ml of hexane was added 0.75 g of tri-n-butyltin hydride and a catalytic amount of 2,2'-azobis (2-methylpropionitrile). This solution was warmed to 50° C. for three hours after which the solvent was removed and the residual materials separated by silica gel chromatography to give 0.72 g of [6S,8R,9S,11R,12S,15R,16R]methyl 6,9-epoxy-11-methyl-16-fluoro-15-hydroxyprost-(13E)-enoate.

EXAMPLE 3

[6S,8R,9S,11R,12S,15R,16R]-6,9-Epoxy-11-methyl-16-fluoro-15-hydroxyprost-(13E)-enoic acid To a solution of 0.7 g of [6S,8R,9S,11R,12S,15R,16R]-methyl 6,9-epoxy-11-methyl-16-fluoro-15-hydroxyprost-(13E)-enoate in 30 ml of dimethoxyethane was added 25 ml of methanol and 8 ml of 1N aqueous sodium hydroxide. After stirring for 2.5 hr. at room temperature, the solvent was removed under reduced pressure and the residue acidified with dilute sulfuric acid. The resultant mixture was extracted with diethyl ether. The combined extracts were dried (MgSO4) and the solvent removed at reduced pressure. The residue was purified by chromatography on Sephadex LH-20 using chloroformhexane (65/35) as the eluent, to yield 0.6 g of [6S,8R,9S,11R,12S,15R,16R]-6,9-epoxy-11-methyl-16-fluoro-hydroxyprost-(13E)enoic acid.

EXAMPLE 4

[6R,8R,9S,11R,12S,15R,16R]Methyl-6,9-epoxy-11-methyl-16-fluoro-15-hydroxyprost-(13E)-enoate By the procedure of Example 2, [5S,6S,8R,9S,11R,12S,15R,16R]methyl 5-iodo-6,9-epoxy-11-methyl-16-fluoro-15-hydroxyprost-(13E)-enoate (4) was converted to [6R,8R,9S,11R,12S,15R,16R]methyl 6,9-epoxy-11-methyl-16-fluoro-15-hydroxyprost-(13E)-enoate.

EXAMPLE 5

[6R,8R,9S,11R,12S,15R,16R]-6,9-Epoxy-11-methyl-16-fluoro-15-hydroxyprost-(13E)-enoic Acid By the procedure of Example 3, [6R,8R,9S,11R,12S,15R,16R]-methyl 6,9-epoxy-11-methyl-16-fluoro-15-hydroxyprost-(13E)-enoate was converted to [6R,8R,9S,11R,12S,15R,16R]-6,9-epoxy-11-methyl-16-fluoro-15-hydroxyprost-(13E)-enoic acid.

EXAMPLE 6

[5R,6R,8R,9S,11R,12S,15R,]-Methyl 5-iodo-6,9-epoxy-11,16,16-trimethyl-15-hydroxyprost-(13E)-enoate, and [5S,6S,8R,11R,12S,15R]Methyl 5-iodo-6,9-epoxy-11,16,16-trimethyl-15-hydroxyprost-(13E)-enoate To an ice cooled, rapidly stirred mixture of 0.45 g of [8R,9S,11R,12S,15R]methyl 11,16,16-trimethyl-9,15-dihydroxyprosta-(5Z),(13E)-dienoate, 5 ml of methylene chloride, and 10 ml of saturated aqueous sodium bicarbonate solution was added dropwise a solution of 0.34 g of iodine in 10 ml of methylene chloride.

After one hour, 30 ml of ethyl ether was added and the layers separated. The organic layer was washed with 10% aqueous sodium thiosulfate and then dried over sodium sulfate. The solvent was removed by rotary evaporation to yield 0.62 g of residual material which upon silica gel chromatography (20% ethyl acetate/hexane as the eluent) yielded 0.42 g of [5R,6R,8R,9S,11R,12S,15R]-methyl 5-iodo-6,9-epoxy-11,16,16-trimethyl-15-hydroxyprost-(13E)-enoate and 0.04 g of [5S,6S,8R,11R,12S,15R]methyl 5-iodo-6,9-epoxy-11,16,16-trimethyl-15-hydroxyprost-(13E)-enoate.

EXAMPLE 7

[6S,8R,9S,11R,12S,15R]Methyl 6,9-epoxy-11,16,16-trimethyl-15-hydroxyprost-(13E)-enoate By the procedure of Example 2, [5R,6R,8R,9S,11R,12S,15R]-methyl 5-iodo-6,9-epoxy-11,16,16-trimethyl-15-hydroxyprost-(13E)-enoate was converted to [6S,8R,9S,11R,12S,15R]-methyl-6,9-epoxy-11,16,16-trimethyl-15-hydroxyprost-(13E)-enoate.

EXAMPLE 8

[6S,8R,9S,11R,12S,15R]6,9-Epoxy-11,16,16-trimethyl-15-hydroxyprost-(13E)-enoic acid By the procedure of Example 3, [6S,8R,9S,11R,12S,15R]methyl 6,9-epoxy-11,16,16-trimethyl-15-hydroxyprost-(13E)-enoate was converted to [6S,8R,9S,11R,12S,15R]-6,9-epoxy-11,16,16-trimethyl-15-hydroxyprost-(13E)-enoic acid.

EXAMPLE 9

[5R,6R,8R,9S,11R,12S,15R]-Methyl 5-iodo-6,9-epoxy-11-methyl-16,16-difluoro-15-hydroxyprost-(13E)-enoate and
[5S,6S,8R,9S,11R,12S,15R]-Methyl 5-iodo-6,9-epoxy-11-methyl-16,16-difluoro-15-hydroxyprost-(13E)-enoate By the procedure of Example 6, [8R,9S,11R,12S,15R]-methyl-11-methyl-16,16-difluoro-9,15-dihydroxyprosta-(5Z),(13E)-dienoate was converted to a mixture of [5R,6R,8R,9S,11R,12S,15R]-methyl 5-iodo-6,9-epoxy-11-methyl-16,16-difluoro-15-hydroxyprost-(13E)-enoate and [5S,6S,8R,11R,12S,15R]-methyl 5-iodo-6,9-epoxy-11-methyl-16,16-difluoro-15-hydroxyprost-(13E)-enoate.

EXAMPLE 10

[6S,8R,9S,11R,12S,15R]-Methyl 6,9-epoxy-11-methyl-16,16-difluoro-15-hydroxyprost-(13E)-enoate By the procedure of Example 2, [5R,6R,8R,9S,11R,12S,15R]-methyl 5-iodo-6,9-epoxy-11-methyl-16,16-difluoro-15-hydroxyprost-(13E)-enoate was converted to [6S,8R,9S,11R,12S,15R]-methyl 6,9-epoxy-11-methyl-16,16-difluoro-15-hydroxyprost-(13E)-enoate.

EXAMPLE 11

[6S,8R,9S,11R,12S,15R]-6,9-Epoxy-11-methyl-16,16-difluoro-15-hydroxyprost-(13E)-enoic acid By the procedure of Example 3, [6S,8R,9S,11R,12S,15R]-methyl 6,9-epoxy-11-methyl-16,16-difluoro-15-hydroxyprost-(13E)-enoate was converted to [6S,8R,9S,11R,12S,15R]-6,9-epoxy-11-methyl-16,16-difluoro-15-hydroxyprost-(13E)-enoic acid.

EXAMPLE 12

By the procedure of Example 1 [8R,9S,11R,12R,15R,16R]-11-carboxy-16-fluoro-9,15-dihydroxyprosta-(5Z),(13E)-dienoic acid was converted to a mixture of [5R,6R,8R,9S,11R,12R,15R,16R]-5-iodo-6,9-epoxy-11-carboxy-16-fluoro-15-hydroxyprost-(13E)-enoic acid and [5S,6S,8R,9S,11R,12R,15R,16R]-5-iodo-6,9-epoxy-11-carboxy-16-fluoro-15-hydroxyprost-(13E)-enoic acid which was esterified and separated by chromatography as described in Example 1 to produce [5R,6R,8R,9S,11R,12R,15R,16R]-methyl-5-iodo-6,9-epoxy-11-carbomethoxy-16-fluoro-15-hydroxyprost-(13E)-enoate and [5S,6S,8R,9S,11R,12R,15R,16R]-methyl-5iodo-6,9-epoxy-11-carbomethoxy-16-fluoro-15-hydroxyprost-13-enoate.

EXAMPLE 13

By the procedure of Example 2 [5R,6R,8R,9S,11R,12R,15R,16R]-methyl-5-iodo-6,9-epoxy-11-carbomethoxy-16-fluoro-15-hydroxyprost-(13E)-enoate was converted to [6S,8R,9S,11R,12R,15R,16R]methyl-6,9-epoxy-11-carbomethoxy-16-fluoro-15-hydroxyprost-(13E)-enoate.

EXAMPLE 14

[6S,8R,9S,11R,12S,15R]6,9-Epoxy-11-carboxy-16-fluoro-15-hydroxyprost-(13E)-enoic acid By the procedure of Example 3, [6S,8R,9S,11R,12S,15R]methyl 6,9-epoxy-11-carbomethoxy-16-fluoro-15-hydroxyprost-(13E)-enoate was converted to [6S,8R,11R,12S,15R]-6,9-epoxy-11-carboxy-16-fluoro-15-hydroxyprost-(13E)-enoic acid.

EXAMPLE 15

[6R,8R,9S,11R,12S,15R,16R]-Methyl 6,9-epoxy-11-carbomethoxy-16-fluoro-15-hydroxyprost-(13E)-enoate By the procedure of Example 2, [5S,6S,8R,9S,11R,12S,15R,16R]-methyl 5-iodo-6,9-epoxy-11-carbomethoxy-16-fluoro-15-hydroxyprost-(13E)-enoate was converted to [6R,8R,9S,12S,15R,16R]-methyl 6,9-epoxy-11-carboxy-16-fluoro-15-hydroxyprost-(13E)-enoate.

EXAMPLE 16

[6S,8R,9S,11R,12S,15R,16R]-6,9-Epoxy-11-carboxy-16-fluoro-15-hydroxyprost-(13E)-enoicacid By the procedure of Example 3, [6S,8R,9S,11R,12S,15R,16R]-methyl 6,9-epoxy-11-carbomethoxy-16-fluoro-15-hydroxyprost-(13E)-enoate was converted to [6S,8R,9S,11R,12S,15R,16R]-6,9-epoxy-11-carboxy-16-fluoro-15-hydroxyprost-(13E)-enoic acid.

EXAMPLE 17

A tablet was prepared containing the following ingredients:

|  | Per Tablet |
|---|---|
| [6S,8R,9S,11R,12S,15R,16R]-6,9-epoxy-11-methyl-16-fluoro-15-hydroxyprost-(13E)-enoic acid | 200 mg. |
| Dicalcium phosphate dihydrate, unmilled | 235 mg. |
| Corn Starch | 70 mg. |
| FD&C Yellow #5-Aluminum Lake 25% | 2 mg. |
| Durkee Duratex* | 25 mg. |
| Calcium Stearate | 3 mg. |
| Total Weight | 535 mg. |

*Hydrogenated cotton seed oil (fully saturated)

All of the above ingredients were mixed until thoroughly blended in a suitable size container. The powder was filled in to #2, two-piece, hard-shell gelatin capsules to an approximate fill weight of 350 mg using a capsulating machine.

EXAMPLE 18

A capsule was prepared by the procedure of example 17 except that [6S,8R,9S,11R,12S,15R]-6,9-epoxy-11-methyl-16,16-difluoro-15-hydroxyprost-(13E)-enoic acid was the active ingredient.

EXAMPLE 19

A capsule was prepared by the procedure of example 17 except [6S,8R,9S,11R,12S,15R]methyl-6,9-epoxy-11,16,16-trimethyl-15-hydroxyprost-(13E)-enoate.

EXAMPLE 20

A tablet was found containing:

|  | Per Tablet |
|---|---|
| [6S,8R,9S,11R,12S,15R,16R]-6,9-epoxy-11-methyl-16-fluoro-15-hydroxyprost-(13E)-enoic acid | 25 mg. |
| Dicalcium phosphate dihydrate, unmilled | 175 mg. |
| Corn Starch | 24 mg. |
| Magnesium stearate | 1 mg. |
| Total Weight | 225 mg. |

The active ingredient and corn starch were mixed together and passed through a #00 screen in Model "J" Fitzmill with hammers forward. This premix was then mixed with dicalcium phosphate and one-half of the magnesium stearate, passed through a #1A screen in Model "J" Fitzmill with knives forward, and slugged. The slugs were passed through a #2A plate in a Model "D" Fitzmill at slow speed with knives forward and the remaining magnesium stearate was added. The mixture was mixed and compressed.

EXAMPLE 21

A tablet was formulated in the same manner as in Example 15 except that [6S,8R,9S,11R,12S,15R]methyl 6,9-epoxy-11,16,16-trimethyl-15-hydroxyprost-(13E)-enoate was the active ingredient.

EXAMPLE 22

A tablet was formulated in the same manner as in example 15 except compound [6R,8R,9S,11R,12S,15R,16R]-methyl 6,9-epoxy-11-carboxy-16-fluoro-15-hydroxyprost-(13E)-enoate was the active ingredient.

EXAMPLE 23

[5R,6R,8R,9S,12R,15R,16R]methyl 5-iodo-6,9-epoxy-16-trifluoromethyl-16-methyl-5-hydroxyprost-(13E)-enoate and [5S,6S,8R,9S,12R,15R,16R]methyl 5-iodo-6,9-epoxy-16-trifluoromethyl-16-methyl-15-hydroxyprost-(13E)-enoate To a solution of 704 mg (1.62 mmol) of [8R,9S,12R,15R,16R]methyl-16-trifluoromethyl-16-methyl-9,15-dihydroxyprosta-(15Z,13E)-dienoate in 10 ml of methylene chloride was added 410 mg of N-iodosuccinimide. After 2 hr., the reaction mixture was diluted with 50 ml of diethyl ether, washed with 10 ml of 2% sodium thiosulfate, and dried (MgSO$_4$). Rotary evaporation of the volatiles yielded 922 mg of oily residuals which upon purification by silica gel chromatography yielded [5S,6R,8R,12R,15R,16R]methyl 5-iodo-6,9-epoxy-16-trifluoromethyl-16-methyl-15-hydroxyprost-(13E)-enoate and [5S,6S,8R,9S,12R,15R,16R]methyl 5-iodo-6,9-epoxy-16-trifluoromethyl-16-methyl-15-hydroxyprost-(13E)-enoate.

EXAMPLE 24

[6S,8R,9S,12R,15R,16R]methyl 6,9-epoxy-16-trifluoromethyl-16-methyl-15-hydroxyprost-(13E)-enoate By the procedure of Example 2, [5R,6R,8R,9S,12R,15R,16R]methyl 5-iodo-6,9-epoxy-16-trifluoromethyl-16-methyl-15-hydroxyprost-(13E)-enoate was converted to [6S,8R,9S,12R,15R,16R]methyl 6,9-epoxy-16-trifluoromethyl-16-methyl-15-hydroxyprost-(13E)-enoate.

EXAMPLE 25

[6S,8R,9S,12R,15R,16R]-6,9-epoxy-16-trifluoromethyl-16-methyl-15-hydroxyprost-(13E)-enoic acid By the procedure of Example 3, [6S,8R,9S,12R,15R,16R]methyl 6,9-epoxy-16-trifluoromethyl-16-methyl-15-hydroxyprost-(13E)-enoate was converted to [6S,8R,9S,12R,15R,16R]-6,9-epoxy-16-trifluoromethyl-16-methyl-15-hydroxyprost-(13E)-enoic acid.

EXAMPLE 26

[5R,6R,8R,9S,11R,12S,15R,16R]methyl-5-iodo-6,9-epoxy-11-hydroxymethyl-16-trifluoromethyl-15-hydroxyprost-(13E)-enoate and [5S,6S,8R,9S,11R,12S,15R,16R]methyl-5-iodo-6,9-epoxy-11-hydroxymethyl-16-trifluoromethyl-15-hydroxyprost-(13E)-enoate By the procedure of Example 23, [8R,9S,11R,12S,15R,16R]methyl-11-hydroxymethyl-16-trifluoromethyl-9,15-dihydroxyprost-(5Z,13E)-dienoate was converted to a mixture of [5R,6R,8R,9S,11R,12S,15R,16R]methyl-5-iodo-6,9-epoxy-11-hydroxymethyl-16-trifluoromethyl-15-hydroxyprost-(13E)-enoate and [5S,6S,8R,9S,11R,12S,15R,16R]methyl-5-iodo-6,9-epoxy-11-hydroxymethyl-16-trifluoromethyl-15-hydroxyprost-(13E)-enoate.

EXAMPLE 27

[6S,8R,9S,11R,12S,15R,16R]methyl-6,9-epoxy-11-hydroxymethyl-16-trifluoromethyl-15-hydroxyprost-(13E)-enoate By the procedure of Example 2, [5R,6R,8R,9S,11R,12S,15R,16R]methyl-5-iodo-6,9-epoxy-11-hydroxymethyl-16-trifluoromethyl-15-hydroxyprost-(13E)-enoate was converted to [6S,8R,9S,11R,12S,15R,16R]methyl-6,9-epoxy-11-hydroxymethyl-16-trifluoromethyl-15-hydroxyprost-(13E)-enoate.

EXAMPLE 28

[6S,8R,9S,11R,12S,15R,16R]-6,9-Epoxy-11-methyl-16-fluoro-15-hydroxyprostanoic acid To a solution of 275 mg of [6S,8R,9S,11R,12S,15R,16R]-6,9-epoxy-11-methyl-16-fluoro-15-hydroxyprost-(13E)-enoic acid in 20 ml of ethyl acetate was added 30 mg of platinum oxide. The mixture was sealed under a positive hydrogen atmosphere and vigorously stirred. After eight hours, the reaction mixture was filtered and the volatiles removed by rotary evaporation. The residual oily product was purified by chromatography over 50 g of Sephadex LH-20 using chloroform-hexane (65/35) to yield [6S,8R,9S,11R,12S,15R,16R]-6,9-epoxy-11-methyl-16-fluoro-15-hydroxyprostanoic acid.

EXAMPLE 29

By the procedure of Example 3, [6S,8R,9S,11R,12S,15R,16R]methyl-6,9-epoxy-11-hydroxymethyl-16-trifluoromethyl-15-hydroxyprost-(13E)-enoate was converted to [6S,8R,9S,11R,12S,15R,16R]-6,9-epoxy-11-hydroxymethyl-16-trifluoromethyl-15-hydroxyprost-(13E)-enoic acid.

EXAMPLE 30

[5R,6R,8R,9S,12R,15R,16R]methyl-5-iodo-6,9-epoxy-16-trifluoromethyl-15-hydroxyprost-(13E)enoate and [5S,6S,8R,9S,12R,15R,16R]methyl-5-iodo-6,9-epoxy-16-trifluoromethyl-15-hydroxyprost-(13E)enoate By the procedure of Example 23, [8R,9S,12R,15R,16R]methyl-16-trifluoromethyl-9,15-dihydroxyprosta-(5Z,13E)-dienoate was converted to [5R,6R,8R,9S,12R,15R,16R]methyl-5-iodo-6,9-epoxy-16-trifluoromethyl-15-hydroxyprost-(13E)-enoate and [5S,6S,8R,9S,12R,15R,16R]methyl-5-iodo-6,9-epoxy-16-trifluoromethyl-15-hydroxyprost-(13E)-enoate.

EXAMPLE 31

[6S,8R,9S,12R,15R,16R]methyl-6,9-epoxy-16-trifluoromethyl-15-hydroxyprost-(13E)-enoate By the procedure of Example 2, [5R,6R,8R,9S,12R,15R,16R]methyl-5-iodo-6,9-epoxy-16-trifluoromethyl-15-hydroxyprost-(13E)-enoate was converted to [6S,8R,9S,12R,15R,16R]methyl-6,9-epoxy-16-trifluoromethyl-15-hydroxyprost-(13E)-enoate.

EXAMPLE 32

[6S,8R,9S,12R,15R,16R]-6,9-Epoxy-16-trifluoromethyl-15-hydroxyprost-(13E)-enoic acid By the procedure of Example 3, [6S,8R,9S,12R,15R,16R]methyl-6,9-epoxy-16-trifluoromethyl-15-hydroxyprost-(13E)-enoate was converted to [6S,8R,9S,12R,15R,16R]-6,9-epoxy-16-trifluoromethyl-15-hydroxyprost-(13E)-enoic acid.

We claim:

1. A compound of the formula:

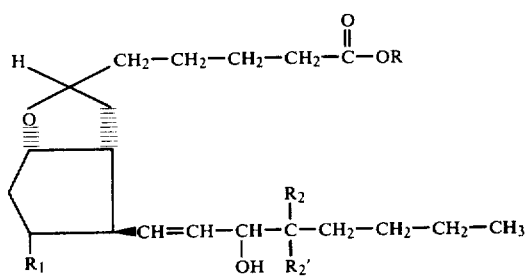

wherein R is hydrogen or lower alkyl; $R_1$ is lower alkyl; $R_2$ is hydrogen, lower alkyl or fluoro; and $R_2'$ is fluoro, trifluoromethyl or lower alkyl; and the dotted bond is optionally hydrogenated and with the proviso that when $R_2$ is fluoro, $R_2'$ is lower alkyl or fluoro and their optical antipodes or racemates.

2. The compound of claim 1 wherein said compound is [6S,8R,9S,11R,12S,15R,16R]-6,9-epoxy-11-methyl-16-fluoro-15-hydroxyprost-(13E)-enoic acid.

3. The compound of claim 1 wherein said compound is [6S,8R,9S,11R,12S,15R]-6,9-epoxy-11-methyl-16,16-difluoro-15-hydroxyprost-(13E)-enoic acid.

4. The compound of claim 1 wherein said compound is [6S,8R,9S,11R,12S,15R]-6,9-epoxy-11,16,16-trimethyl-15-hydroxyprost-(13E)-enoic acid.

5. A compound of the formula:

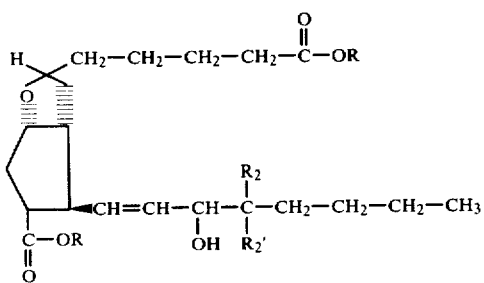

wherein R is hydrogen or lower alkyl; $R_2$ is hydrogen, lower alkyl or fluoro; and $R_2'$ is fluoro, trifluoromethyl or lower alkyl; and the dotted bond is optionally hydrogenated and with the proviso that when $R_2$ is fluoro, $R_2'$ is lower alkyl or fluoro and their optical antipodes or racemates.

6. The compound of claim 5 wherein said compound is [6S,8R,9S,11R,12R,15R,16R]-methyl-6,9-epoxy-11-carbomethoxy-16-fluoro-15-hydroxyprost-(13E)-enoate.

7. The compound of claim 5 wherein said compound [6S,8R,9S,11R,12R,15R,16R]-6,9-epoxy-11-carboxy-16-fluoro-15-hydroxyprost-(13E)-enoic acid.

8. A compound of the formula:

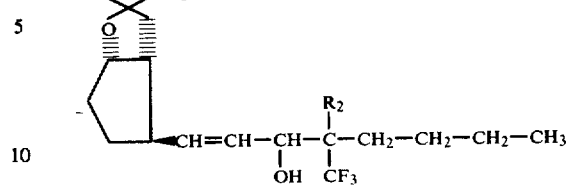

wherein R is hydrogen or lower alkyl; $R_2$ is hydrogen or lower alkyl; and the dotted bond can be optionally hydrogenated, and its optical antipodes or racemates.

9. The compound of claim 8 wherein said compound is [6S,8R,9S,12R,15R,16R]-6,9-epoxy-16-trifluoromethyl-16-methyl-15-hydroxyprost-(13E)-enoic acid.

10. A compound of the formula:

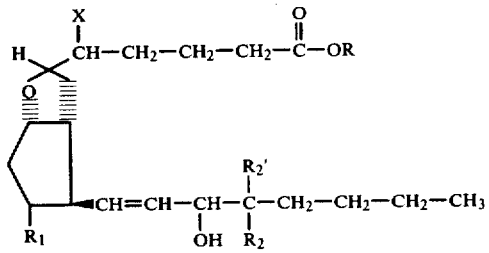

wherein R is hydrogen or lower alkyl; $R_1$ is lower alkyl; $R_2$ is lower alkyl, hydrogen or fluoro; $R_2'$ is fluoro, trifluoromethyl or lower alkyl; and X is halogen and with the proviso that when $R_2$ is fluoro, $R_2'$ is fluoro or lower alkyl and their optical antipodes or racemates.

11. The compound of claim 10 wherein said compound is [5S,6S,8R,9S,11R,12R,15R,16R]-5-iodo-6,9-epoxy-11-methyl-16-fluoro-15-hydroxyprost-(13E)-enoic acid.

12. The compound of claim 10 wherein said compound is [5S,6S,8R,9S,11R,12S,15R,16R]methyl-5-iodo-6,9-epoxy-11-methyl-16-fluoro-15-hydroxyprost-(13E)-enoate.

13. The compound of claim 10 wherein said compound is [5R,6R,8R,9S,11R,12S,15R,16R]methyl-5-iodo-6,9-epoxy-11-methyl-16-fluoro-15-hydroxyprost-(13E)-enoate.

14. The compound of claim 10 wherein said compound is [5S,6S,8R,9S,11R,12S,15R]methyl-5-iodo-6,9-epoxy-11,16,16-trimethyl-15-hydroxyprost-(13E)-enoate.

15. The compound of the formula:

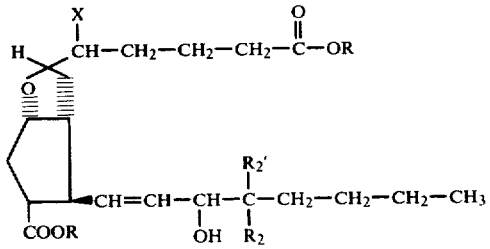

wherein R is hydrogen or lower alkyl; $R_2$ is lower alkyl, hydrogen or fluoro; $R_2'$ is fluoro, trifluoromethyl or lower alkyl; and X is halogen and with the proviso that when $R_2$ is fluoro, $R_2'$ is fluoro or lower alkyl and their optical antipodes or racemates.

16. The compound of claim 15 wherein said compound is [5R,6R,8R,9S,11R,12S,15R,16R]-5-iodo-6,9-epoxy-11-carboxy-16-fluoro-15-hydroxyprost-(13E)-enoic acid.

17. The compound of claim 15 wherein said compound is [5R,6R,8R,9S,11R,12R,15R,16R]methyl-5-iodo-6,9-epoxy-11-carbomethoxy-16-fluoro-15-hydroxyprost-(13E)-enoat.

* * * * *